(12) United States Patent
Lee et al.

(10) Patent No.: US 9,076,956 B2
(45) Date of Patent: Jul. 7, 2015

(54) SAW ARRAY SENSOR

(71) Applicant: Samsung Electronics Co., Ltd., Suwon-si, Gyeonggi-do (KR)

(72) Inventors: Yeol-ho Lee, Seoul (KR); Youn-suk Choi, Yongin-si (KR); Tae-han Lee, Yongin-si (KR); Soo-suk Lee, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 264 days.

(21) Appl. No.: 13/743,152

(22) Filed: Jan. 16, 2013

(65) Prior Publication Data

US 2014/0001918 A1    Jan. 2, 2014

(30) Foreign Application Priority Data

Jun. 27, 2012 (KR) .................. 10-2012-0069475

(51) Int. Cl.
| | | |
|---|---|---|
| *H03H 9/42* | (2006.01) | |
| *H01L 41/047* | (2006.01) | |
| *H03H 9/145* | (2006.01) | |
| *G01N 29/02* | (2006.01) | |
| *G01N 29/32* | (2006.01) | |

(52) U.S. Cl.
CPC ............. *H01L 41/0475* (2013.01); *H03H 9/42* (2013.01); *H03H 9/14544* (2013.01); *G01N 29/022* (2013.01); *G01N 29/32* (2013.01); *G01N 2291/106* (2013.01)

(58) Field of Classification Search
CPC .. H01L 41/0475; G01N 29/022; G01N 29/32; G01N 2291/106; H03H 9/14502; H03H 9/14544; H03H 9/42
USPC .................. 333/150–154; 310/313 R, 313 B; 73/24.06, 61.75, 64.53, 649
See application file for complete search history.

(56) References Cited

U.S. PATENT DOCUMENTS

| | | | | |
|---|---|---|---|---|
| 4,237,432 A | * | 12/1980 | Huang et al. ................... | 333/194 |
| 4,598,224 A | * | 7/1986 | Ballato ...................... | 310/313 R |
| 5,325,704 A | * | 7/1994 | Mariani et al. ................ | 73/24.06 |
| 7,100,451 B2 | * | 9/2006 | Solie ............................... | 73/703 |
| 7,500,379 B2 | * | 3/2009 | Hines ........................... | 73/24.06 |

(Continued)

FOREIGN PATENT DOCUMENTS

| | | |
|---|---|---|
| GB | 2029148 A | 3/1980 |
| JP | 62-190905 A | 8/1987 |

(Continued)

OTHER PUBLICATIONS

Josse et al.; "Guided SH-SAW Sensors for Liquid-Phase Detection"; 2001 IEEE International Frequency Control Symposium and PDA Exhibition, Jun. 6-8, 2001, pp. 454-461.*

(Continued)

*Primary Examiner* — Barbara Summons
(74) *Attorney, Agent, or Firm* — Leydig, Voit & Mayer, Ltd.

(57) ABSTRACT

A surface acoustic wave (SAW) array sensor having an input interdigital transducer (IDT); first and second output IDTs that are disposed at both sides of the input IDT, respectively; a first delay line between the input IDT and the first output IDT; and a second delay line between the input IDT and the second output IDT, wherein the first and second delay lines have different lengths; and related devices.

19 Claims, 9 Drawing Sheets

(56) References Cited

U.S. PATENT DOCUMENTS

| | | | |
|---|---|---|---|
| 7,598,653 B2 * | 10/2009 | Tsai et al. | 310/313 R |
| 7,633,206 B2 | 12/2009 | Andle et al. | |
| 7,755,250 B2 | 7/2010 | Bruckner et al. | |
| 7,771,987 B2 * | 8/2010 | Edmonson et al. | 435/287.2 |
| 2006/0049714 A1 * | 3/2006 | Liu et al. | 310/313 R |
| 2006/0213271 A1 * | 9/2006 | Edmonson et al. | 73/579 |
| 2007/0159027 A1 | 7/2007 | Tsai et al. | |
| 2007/0164633 A1 * | 7/2007 | Cobianu et al. | 310/313 A |
| 2007/0296305 A1 * | 12/2007 | Hines et al. | 310/313 B |
| 2010/0058834 A1 | 3/2010 | Cobianu et al. | |
| 2011/0068656 A1 | 3/2011 | Lee et al. | |
| 2012/0105174 A1 | 5/2012 | Lee et al. | |

FOREIGN PATENT DOCUMENTS

| | | |
|---|---|---|
| JP | 2008-286521 A | 11/2008 |
| JP | S58161412 A | 10/2013 |
| KR | 1020110032239 A | 3/2011 |

OTHER PUBLICATIONS

European Patent Office, Extended European Search Report in European Patent Application No. 13163444.6, Feb. 7, 2014, 8 pp.

European Search Report, European Application No. 13163444.6, dated Oct. 14, 2013.

* cited by examiner

<br>

SAW ARRAY SENSOR

CROSS-REFERENCE TO RELATED APPLICATIONS

This application claims the benefit of Korean Patent Application No. 10-2012-0069475, filed on Jun. 27, 2012, in the Korean Intellectual Property Office, the disclosure of which is incorporated herein in its entirety by reference.

BACKGROUND

A surface acoustic wave (SAW) sensor is a device that may be used to analyze a particular target material in a sample by using a SAW. A SAW is an acoustic wave that travels along the surface of a material, and can be generated when particles in the material vibrate due to an external thermal, mechanical, or electrical force. A SAW exhibits vibration energy that is mostly concentrated on the surface of the material. The movement of a SAW in a material is affected by one or more properties of the material. A SAW sensor can be used to analyze a target material by sensing a change in a SAW caused by a change in a property of the material. For example, a change in intensity, phase, or central wavelength of the SAW may indicate the presence of a particular target material.

A conventional SAW sensor may include a substrate formed of a piezoelectric material, an input interdigital transducer (IDT) that generates a SAW by applying an electrical stimulus to the substrate, and an output IDT that receives the SAW. In the SAW sensor, a portion between the input IDT and the output IDT in which the SAW travels is generally referred to as a delay line. A receptor having a specific binding with a desired particular target material may be disposed on a path on which the SAW travels on the substrate, for example, in the delay line.

When a SAW is generated in the SAW sensor having the above structure and a sample including a target material is applied to the SAW sensor, the target material may combined with the receptor and change an intensity, phase, or central wavelength of the SAW that is received from the output IDT. Thus, by sensing a change in the SAW, it may be determined whether the target material exists in the sample, and the content of the target material in the sample may be precisely measured.

A SAW array sensor may be configured by arranging a plurality of SAW sensors on one substrate. By using a SAW array sensor, various types of receptors may be disposed on the substrate, so as to analyze various components of the sample at one time. The SAW array sensor can suppress cross-talk that is generated due to a reflected wave generated in adjacent delay lines, and simultaneously, the size of the SAW array sensor may be reduced.

SUMMARY

Provided are surface acoustic wave (SAW) array sensors having improved sensitivity by removing cross-talk between SAW sensors.

Additional aspects will be set forth in part in the description which follows and, in part, will be apparent from the description, or may be learned by practice of the presented embodiments.

According to an aspect of the present invention, a surface acoustic wave (SAW) array sensor includes: an input interdigital transducer (IDT); first and second output IDTs that are disposed at both sides of the input IDT, respectively; a first delay line between the input IDT and the first output IDT; and a second delay line between the input IDT and the second output IDT, wherein the first and second delay lines have different lengths.

The input IDT, the first and second output IDTs, and the first and second delay lines may be arranged in a same line along a traveling direction of a SAW.

A receptor having a specific binding with a target material in a sample may be disposed on each of the first and second delay lines.

The SAW array sensor may include a plurality of SAW sensor units that are arranged on one piezoelectric substrate, and each of the plurality of SAW sensor units may include the input IDT, the first and second output IDTs, and the first and second delay lines, which are arranged in a same line along a travelling direction of a SAW.

The plurality of SAW sensor units may be arranged along a direction that is perpendicular to the traveling direction of the SAW.

A receptor having a specific binding with a target material in a sample may be disposed in each of the first and second delay lines of the plurality of SAW sensor units.

A length of the first delay line and a length of the second delay line in adjacent SAW sensor units may be reversed.

According to another aspect of the present invention, a surface acoustic wave (SAW) array sensor includes: first and second input interdigital transducers (IDTs) that face each other; a first output IDT that is disposed adjacent to a side surface of the first input IDT; a second output IDT that is disposed adjacent to a side surface of the second input IDT; a first delay line between the first input IDT and the first output IDT; and a second delay line between the second input IDT and the second output IDT, wherein the first and second input IDTs are configured so that a SAW generated in the first input IDT and a SAW generated in the second input IDT have a phase difference of 180 degrees out of phase so that the SAW generated in the first input IDT and the SAW generated in the second input IDT are cancelled out at the location between the first input IDT and the second input IDT.

The first input IDT and the second input IDT may be axially symmetrical to each other, and voltages having same polarities may be applied to electrodes disposed at same sides of the first input IDT and the second input IDT.

The first input IDT and the second input IDT may be rotational symmetric about each other, and voltages having different polarities may be applied to electrodes disposed at same sides of the first input IDT and the second input IDT.

The first and second delay lines may have different lengths.

A receptor having a specific binding with a target material in a sample may be disposed on each of the first and second delay lines.

The input IDT, the first and second output IDTs, and the first and second delay lines may be arranged in a same line along a traveling direction of a SAW.

The SAW array sensor may include a plurality of SAW sensor units that are arranged on one piezoelectric substrate, and each of the plurality of SAW sensor units may include the input IDT, the first and second output IDTs, and the first and second delay lines, which are arranged in a same line along a travelling direction of a SAW.

The plurality of SAW sensor units may be arranged along a direction that is perpendicular to the traveling direction of the SAW.

A receptor having a specific binding with a target material in a sample may be disposed on each of the first and second delay lines of the plurality of SAW sensor units.

The first and second delay lines may have different lengths.

A distance between the first and second input IDTs and lengths of the first and second delay lines may be different from one another.

A length of the first delay line and a length of the second delay line in adjacent SAW sensor units may be reversed.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
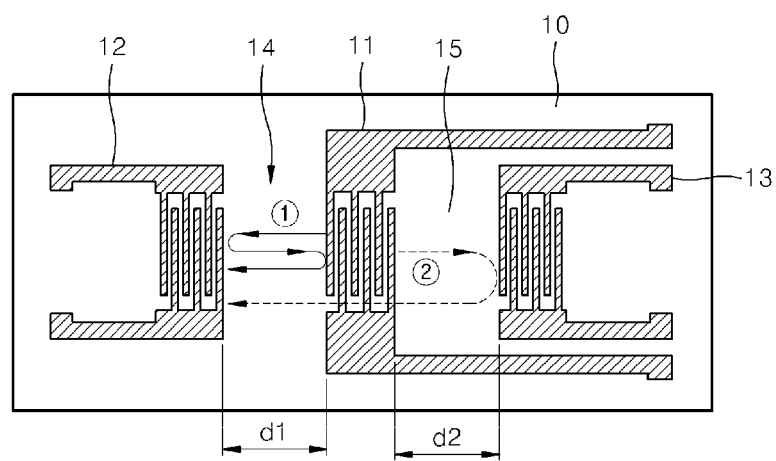
FIG. 1 is a schematic plan view of the principle of a surface acoustic wave (SAW) array sensor.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. In addition, an expression, such as "above" or "on", in the following layer structure may involve the case where an element or layer is referred to as being directly on another element or layer in a contact manner or being above another element or layer in a noncontact manner.

FIG. 1 is a schematic plan view of the principle of a surface acoustic wave (SAW) array sensor according to an example embodiment.

Referring to FIG. 1, the SAW array sensor according to the current embodiment may include an input interdigital transducer (IDT) 11, a first output IDT 12, and a second output IDT 13, which are disposed on a piezoelectric substrate 10. Each of the input IDT 11, the first output IDT 12, and the second output IDT 13 has two electrodes in which a plurality of protruding thin finger-like portions ("fingers") are interdigitated. When voltages are applied to two electrodes of the input IDT 11, the piezoelectric substrate 10 vibrates due to an electrical stimulus and thus a SAW is generated. A wavelength of the SAW generated in this way may be determined by a finger pitch of the input IDT 11, and the number of waves of the SAW may be proportional to the number of fingers of the input IDT 11. The SAW generated in the input IDT 11 travels along the surface of the piezoelectric substrate 10 in two directions of the input IDT 11, i.e., in right and left directions of the input IDT 11 as shown in FIG. 1.

A section between the input IDT 11 and the first output IDT 12 is a first delay line 14 via which the SAW reaches the first output IDT 12. In addition, a section between the input IDT 11 and the second output IDT 13 is a second delay line 15 via which the SAW reaches the second output IDT 13. The "delay line" is the separation between the IDTs, and the "length" of the delay line is the distance between the IDTs. Thus, as illustrated in FIG. 1, the input IDT 11, the first and second output IDTs 12 and 13, and the first and second delay lines 14 and 15 are arranged in the same line (aligned with one another, such as in a row) along a traveling direction of the SAW. A receptor (not shown) having a specific binding with a target material in a sample may be disposed on one or both of the first and second delay lines 14 and 15. Any suitable receptor can be used, such as a receptor for a biological material (e.g., antibody, protein, aptamer, nucleic acid, etc.).

In the above structure of the SAW array sensor, while the SAW traveling to the left of the input IDT 11 passes through the first delay line 14, an intensity, a phase, or a central wavelength of the SAW may vary according to the amount of target material combines with the receptor disposed on the first delay line 14. Similarly, while the SAW traveling to the right of the input IDT 11 passes through the second delay line 15, an intensity, a phase, or a central wavelength of the SAW may vary according to the amount of target material that combines with the receptor disposed on the second delay line 15. Thus, the SAW array sensor according to the present embodiment may perform analysis of two independent target materials simultaneously and thus the size of the SAW array sensor may be reduced compared to conventional SAW array sensors.

However, since the input IDT 11, the first and second output IDTs 12 and 13, and the first and second delay lines 14 and 15 are arranged in the same line along the traveling direction of the SAW, there is a possibility that cross-talk of signals may occur when the SAW traveling to the right of the input IDT 11 is reflected by the second output IDT 13 and then reaches the first output IDT 12. Similarly, there is a possibility that cross-talk of signals may occur when the SAW traveling to the left of the input IDT 11 is reflected by the first output IDT 12 and then reaches the second output IDT 13. The cross-talk introduced by the reflected waves that are generated in the two adjacent delay lines 14 and 15 may disturb precise analysis of the target materials.

For example, the SAW that reaches the first output IDT 12 may include a SAW that directly comes from the input IDT 11, a SAW that is reflected by the first output IDT 12 and then is re-reflected by the input IDT 11 (indicated by '①' in FIG. 1, the SAW is referred to as, in particular, a triple transient echo (TTE)), a SAW that is reflected between the first output IDT 12 and the input IDT 11 three or more times, and a SAW that is reflected by the second output IDT 13 (indicated by '②' in FIG. 1). There is a large possibility that the SAW that is reflected by the second output IDT 13 and then reaches the first output IDT 12 may interfere with a TTE signal, in particular, when a length d1 of the first delay line 14 and a length d2 of the second delay line 15 are the same.

Figure 2:
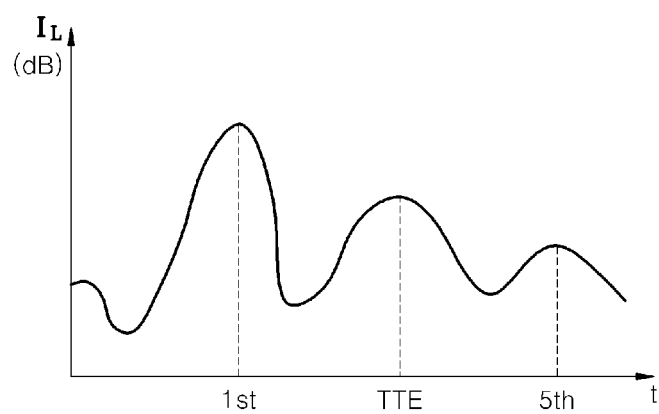
FIG. 2 is a graph showing signals that reach an output interdigital transducer (IDT) when a reflected wave is not generated in adjacent delay lines.

FIG. 2 is a graph showing signals that reach the first output IDT 12 when a reflected wave is not generated in the second delay line 15. In the graph of FIG. 2, the vertical axis represents an insertion loss (IL) indicated in units of dB, and the horizontal axis represents time. Referring to the graph of FIG. 2, a first peak is generated due to the SAW that directly comes from the input IDT 11, and a second peak is generated due to the TTE signal that is reflected by the first output IDT 12 and then is re-reflected by the input IDT 11. Since the TTE signal passes three times through the first delay line 14 on which the receptor is disposed until the TTE signal reaches the first output IDT 12, a change in the TTE signal at the second peak is larger than a change in the SAW at the first peak at which the SAW passes through the first delay line 14 only once. A change in a signal at a third peak at which the SAW passes through the first delay line 14 five times is larger than a change in the TTE signal at the second peak, but an intensity of the SAW is much smaller than an intensity of the TTE signal. For these reasons, the TTE signal is used as a signal for analyzing a target material in the sample.

Figure 3:
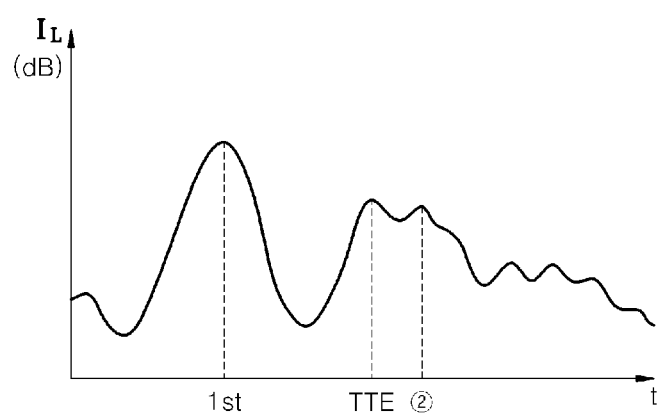
FIG. 3 is a graph showing signals that reach an output IDT when a reflected wave is generated in adjacent delay lines when lengths of two delay lines are the same.

FIG. 3 is a graph showing signals that reach the first output IDT 12 when a reflected wave is generated in the second delay line 15 when lengths of the two delay lines, namely, the first and second delay lines 14 and 15, are the same. The length of a path on which a SAW is reflected by the second output IDT 13 and then reaches the first output IDT 12 is nearly the same as that of the TTE signal. Thus, as indicated by the graph of FIG. 3, a SAW (indicated by '②' in FIG. 1) that is reflected by the second output IDT 13 may reach the first output IDT 12 at a time that is almost the same a time at which the TTE signal reaches the first output IDT 12. Thus, the signal reflected by the second output IDT 13 and the TTE signal may not be discriminated from each other, and thus a precise analysis may not be easily performed.

Thus, in order to remove or minimize cross-talk that is generated by the signal reflected by the second output IDT 13 in the present embodiment, the length d1 of the first delay line 14 and the length d2 of the second delay line 15 are designed to be different from each other. Since the TTE signal is important in analysis of the sample, the signal that is reflected by the second output IDT 13 reaches the first output IDT 12 sufficiently prior to or later than the TTE signal, or the signal reflected by the first output IDT 12 reaches the second output IDT 13 sufficiently prior to or later than the TTE signal, so as to identify the TTE signal.

Figure 4:
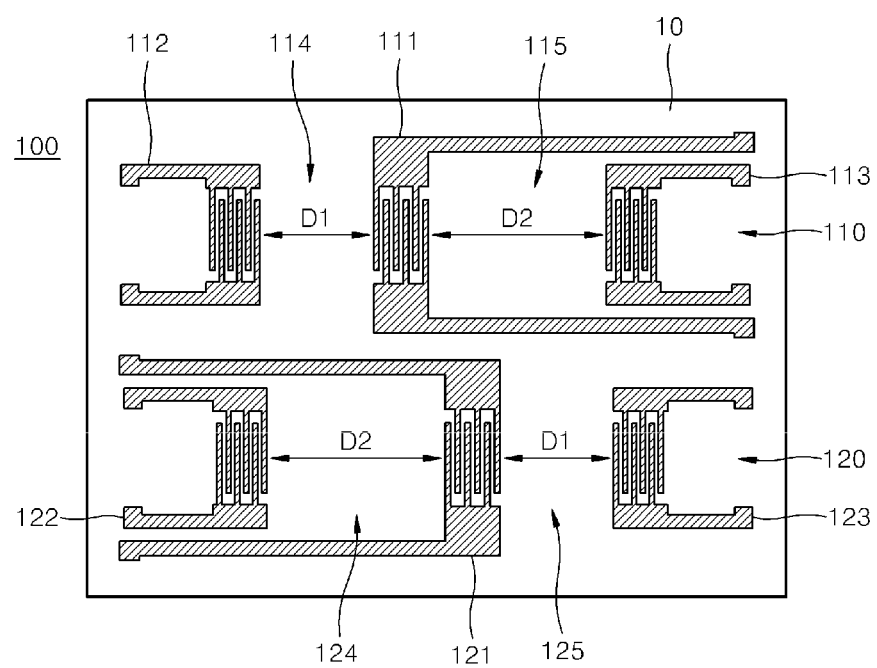
FIG. 4 is a schematic plan view of a SAW array sensor.

FIG. 4 is a schematic plan view of a SAW array sensor 100 according to another example embodiment. Referring to FIG. 4, the SAW array sensor 100 may include a plurality of SAW sensor units 110 and 120 that are arranged on a single piezoelectric substrate 10. Although, for convenience of explanation, two SAW sensor units 110 and 120 are shown in FIG. 4, three or more SAW sensor units may be arranged on the piezoelectric substrate 10. As depicted in FIG. 4, the SAW sensor units 110 and 120 may be adjacent and arranged along a direction that is generally perpendicular to the direction a SAW produced by units 110 or 120 travels, i.e., to the right and left in FIG. 4.

The first SAW sensor unit 110 may include an input IDT 111, first and second output IDTS 112 and 113 that are disposed at both sides of the input IDT 111, a first delay line 114 between the input IDT 111 and the first output IDT 112, and a second delay line 115 between the input IDT 111 and the second output IDT 113. In other words, the input IDT is positioned between the first and second output IDTs. Here, the length D1 of the first delay line 114 and the length D2 of the second delay line 115 are different from each other. As described above, the input IDT 111, the first and second output IDTs 112 and 113, and the first and second delay lines 114 and 115 are arranged in the same line along the traveling direction of the SAW. In addition, a receptor (not shown) having a specific binding with a target material in a sample may be disposed on each of the first and second delay lines 114 and 115.

Similarly, the second SAW sensor unit 120 may include an input IDT 121, first and second output IDTs 122 and 123 that are disposed at both sides of the input IDT 121, respectively, a first delay line 124 between the input IDT 121 and the first output IDT 122, and a second delay line 125 between the input IDT 121 and the second output IDT 123. Here, a length D2 of the first delay line 124 and a length D1 of the second delay line 125 are different from each other.

As illustrated in FIG. 4, lengths of the first and second delay lines 114 and 115 of the first SAW sensor unit 110 are D1 and D2, respectively, and lengths of the first and second delay lines 124 and 125 of the second SAW sensor unit 120 are D2 and D1, respectively. That is, lengths of the first delay lines 114 and 124 of the adjacent SAW sensor units 110 and 120 and lengths of the second delay lines 115 and 125 may be reversed. In other words, the delay lines of adjacent SAW sensor units may have different lengths. Furthermore, the lengths of the delay lines of adjacent SAW sensor units may alternate. For instance, a first SAW unit sensor may have a first delay line with length X and a second delay line with length Y; a second SAW unit sensor adjacent to the first SAW unit sensor may have a first delay line with length Y, and a second delay line with length X; a third SAW unit sensor adjacent to the second SAW unit sensor may have a first delay line with a length X and a second delay line with length Y, and so on. However, this is just an example, and the lengths of the first delay lines 114 and 124 may be the same, and the lengths of the second delay lines 115 and 125 may be the same in other embodiments.

Figure 5:
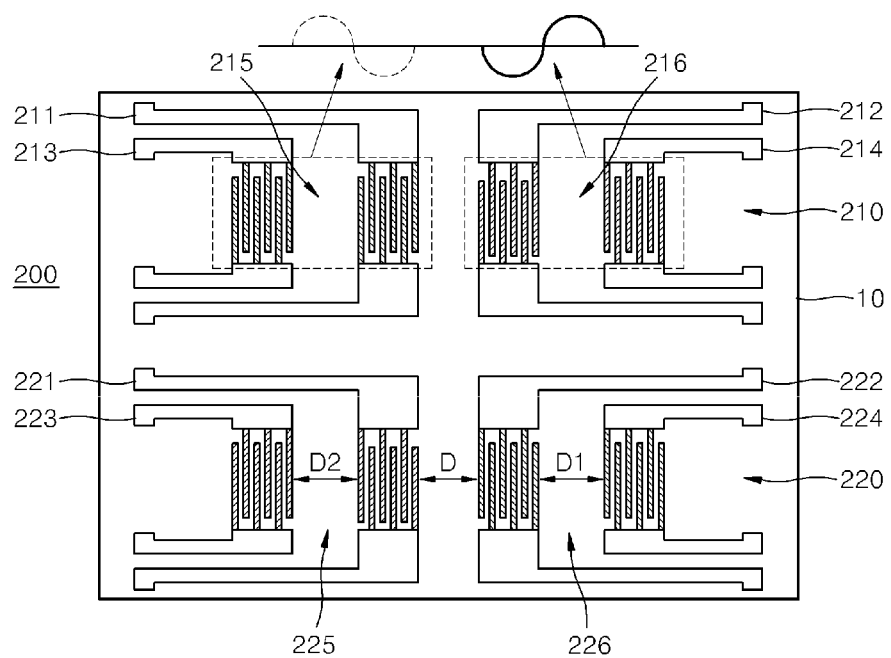
FIG. 5 is a schematic plan view of a SAW array sensor.

FIG. 5 is a schematic plan view of a SAW array sensor 200 according to another example embodiment. Referring to FIG. 5, the SAW array sensor 200 may include a plurality of SAW sensor units 210 and 220 that are arranged on one piezoelectric substrate 10. Although, for convenience of explanation, only two SAW sensor units 210 and 220 are shown in FIG. 5, three or more SAW sensor units may be arranged on one piezoelectric substrate. The plurality of SAW sensor units 210 and 220 may be adjacent and arranged along a direction that is generally perpendicular to the direction a SAW produced by units 210 or 220 travels, i.e., to the right and left in FIG. 5.

Each of the SAW sensor units 210 and 220 may include two input IDTs 211, 212, 221, and 222, and two output IDTs 213, 214, 223, and 224. For example, the first SAW sensor unit 210 may include first and second input IDTs 211 and 212 that face each other, a first output IDT 213 that is disposed adjacent to a side surface of the first input IDT 211, a second output IDT 214 that is disposed adjacent to a side surface of the second input IDT 212, a first delay line 215 between the first input IDT 211 and the first output IDT 213, and a second delay line 216 between the second input IDT 212 and the second output IDT 214. Here, the first and second input IDTs 211 and 212, the first and second output IDTs 213 and 214, and the first and second delay lines 215 and 216 may be arranged in the same line along the traveling direction of the SAW.

Similarly, the second SAW sensor unit 220 may include first and second input IDTs 221 and 222 that face each other, a first output IDT 223 that is disposed adjacent to the side surface of the first input IDT 221, a second output IDT 224 that is disposed adjacent to the side surface of the second input IDT 222, a first delay line 225 between the first input IDT 221 and the first output IDT 223, and a second delay line 226 between the second input IDT 222 and the second output IDT 224.

In the present embodiment, two input IDTs 211 and 212 are disposed in the first SAW sensor unit 210, and two input IDTs 221 and 222 are disposed in the second SAW sensor unit 220. For example, in the first SAW sensor unit 210, cross-talk between a first SAW—which is generated in the first input IDT 211 and passes through the first delay line 215 to reach the first output IDT 213—and a second SAW—which is generated in the first input IDT 211, passes through the second input IDT 212 and the second delay line 216, and is reflected by the second output IDT 214 to reach the first output IDT 213—may be generated. In addition, cross-talk between a first SAW—which is generated in the first input IDT 211 and passes through the second input IDT 212 and the second delay line 216 to reach the second output IDT 214—and a second SAW—which is generated in the second input IDT 212 and reaches the second output IDT 214—may be generated.

In the present embodiment, in order to prevent such cross-talk, the SAW generated in the first input IDT 211 and the SAW generated in the second input IDT 212 may be cancelled in a space between the first input IDT 211 and the second input IDT 212. For example, the first and second input IDTs 211 and 212 may be configured in such a way that the SAW generated in the first input IDT 211 and the SAW generated in the second input IDT 212 may have a phase difference of about 180 degrees. Then, the SAWs that are generated in the first and second input IDTs 211 and 212 may be cancelled in a space between the first and second input IDTs 211 and 212 and may be extinguished before the SAWS are transferred to the first and second output IDTs 213 and 214. As a result, the SAW that is generated in the first input IDT 211 may only reach the first output IDT 213, and the SAW that is generated in the second input IDT 212 may only reach the second output IDT 214. The first input IDT 211 and the second input IDT 212 may be simultaneously turned on/off so that the SAWs generated in two input IDTs 211 and 212 may be precisely canceled.

Figure 6A:
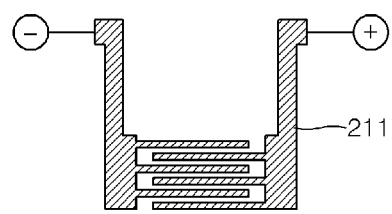
FIGS. 6A and 6B are schematic plan views of an electrode structure of an input IDT illustrated in FIG. 5.
Figure 6A:
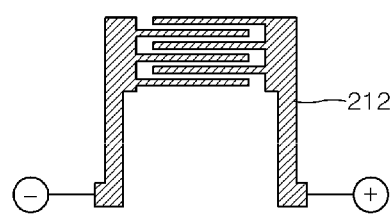

Phases of the SAWs generated in the input IDTs 211 and 212 may be determined by the arrangement of fingers of the input IDTs 211 and 212, and the polarity of applied voltages. For example, referring to FIG. 6A, the first input IDT 211 and the second input IDT 212 may be axially symmetric to each other. In this respect, axial symmetry means symmetry about an axis in the x-y plane of the surface of the piezoelectric substrate on which the IDTs are disposed that extends in a direction perpendicular to the direction of SAW propagation from the input IDT to the output IDT. Fingers in the right electrodes (as depicted in FIG. 6A) of the first and second input IDTs 211 and 212 may be disposed at a front of the SAW array sensor 200. In another embodiment, fingers in left electrodes (as depicted in FIG. 6A) of the first and second input IDTs 211 and 212 may be disposed at the front of the SAW array sensor 200. In this case, when voltages having the same polarity are applied to electrodes disposed at the same sides of the first input IDT 211 and the second input IDT 212 of FIG. 6A relative to a line bisecting the IDTs in a direction parallel to SAW propogation, SAWs having a phase difference of about 180 degrees may be generated in the first input IDT 211 and the second input IDT 212. For example, in FIG. 6A, positive voltages are applied to right electrodes of the first input IDT 211 and the second input IDT 212, and negative voltages are applied to left electrodes of the first input IDT 211 and the second input IDT 212. Alternatively, negative voltages may be applied to the right electrodes of the first input IDT 211 and the second input IDT 212, and positive voltages may be applied to the left electrodes of the first input IDT 211 and the second input IDT 212.

Figure 6B:
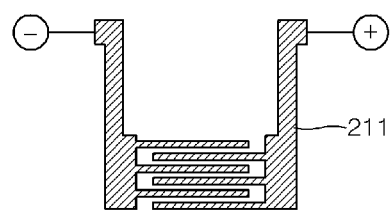
Figure 6B:
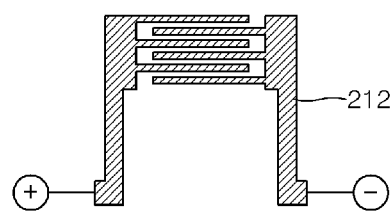

FIG. 6B illustrates another example embodiment. In FIG. 6B the first input IDT 211 and the second input IDT 212 may be rotational symmetric about each other. In this respect, rotational symmetry means symmetry about an axis perpendicular to the x-y plane of the surface of the piezoelectric substrate on which the IDTs are disposed and centrally positioned between the IDTs. Fingers in the right electrodes (as depicted in FIG. 6B) of the first input IDT 211 may be disposed at the front of the SAW array sensor 200, and fingers in the left electrodes (as depicted in FIG. 6B) of the second input IDT 212 may be disposed at the front of the SAW array sensor 200. Alternatively, the fingers in the left electrodes of the first input IDT 211 may be disposed at the front of the SAW array sensor 200, and the fingers in the right electrodes of the second input IDT 212 may be disposed at the front of the SAW array sensor 200. In either case, when voltages having opposite polarity are applied to the electrodes disposed at the same sides of the first input IDT 211 and the second input IDT 212 of FIG. 6B, SAWs having a phase difference of about 180 degrees may be generated in the first input IDT 211 and the second input IDT 212. For example, in FIG. 6B, positive voltages are applied to the right electrodes of the first input IDT 211, and negative voltages are applied to the right electrodes of the second input IDT 212. Alternatively, negative voltages may be applied to the right electrodes of the first input IDT 211, and positive voltages may be applied to the right electrodes of the second input IDT 212.

Providing for the case that only one of the first input IDT 211 and the second input IDT 212 is turned on, lengths of the first delay line 215 and the second delay line 216 may be different from each other. Referring to FIG. 5, a distance between the first input IDT 221 and the second input IDT 222 is D, a length of the first delay line 225 between the first input IDT 221 and the first output IDT 223 is D2, and a length of the second delay line 226 between the second input IDT 222 and the second output IDT 224 is D1. In this way, the distance between the first input IDTs 221 and 222 and the lengths of the first and second delay lines 225 and 226 are different from one another so that a cross-talk caused by a reflected wave may be reduced. In this case, even when the first input IDT 211 and the second input IDT 212 are simultaneously turned on, the effect of reflection of a SAW that is not canceled and remains may be reduced. In addition, as in FIG. 4, in adjacent SAW sensor units 210 and 220, the lengths of the first delay lines 215 and 225 and the lengths of the second delay lines 216 and 226 may be the same or different.

Figure 7:
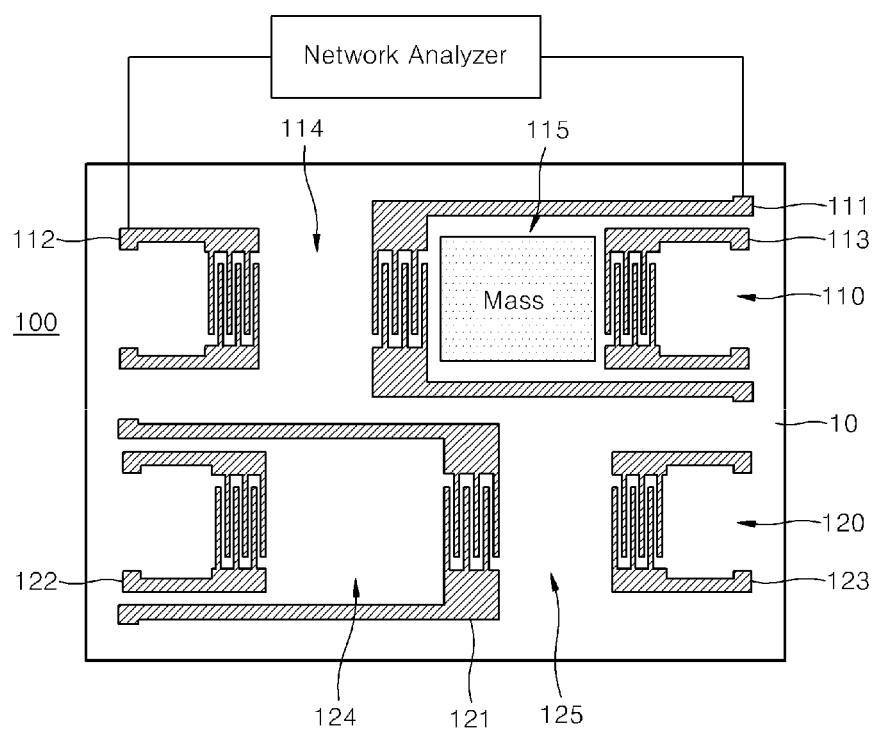
FIG. 7 is a schematic plan view of an arrangement for checking operating characteristics of the SAW array sensor illustrated in FIG. 4.
Figure 8:
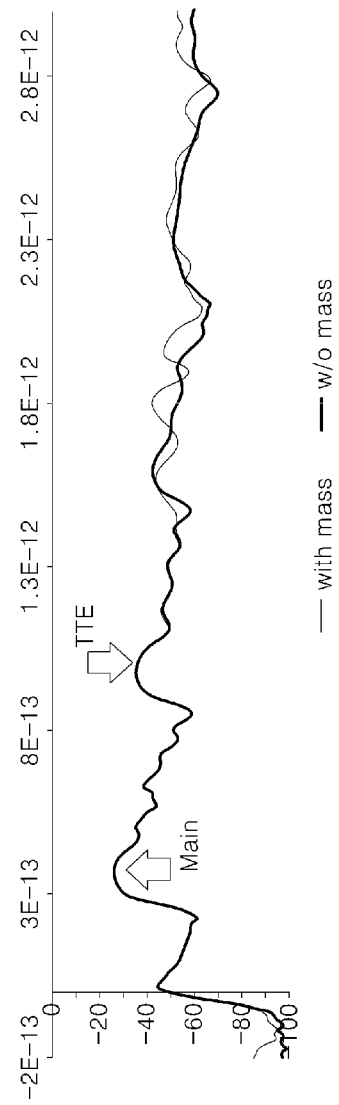
FIG. 8 is a graph showing operating characteristics of a SAW array sensor according to the arrangement of FIG. 7.
Figure 9:
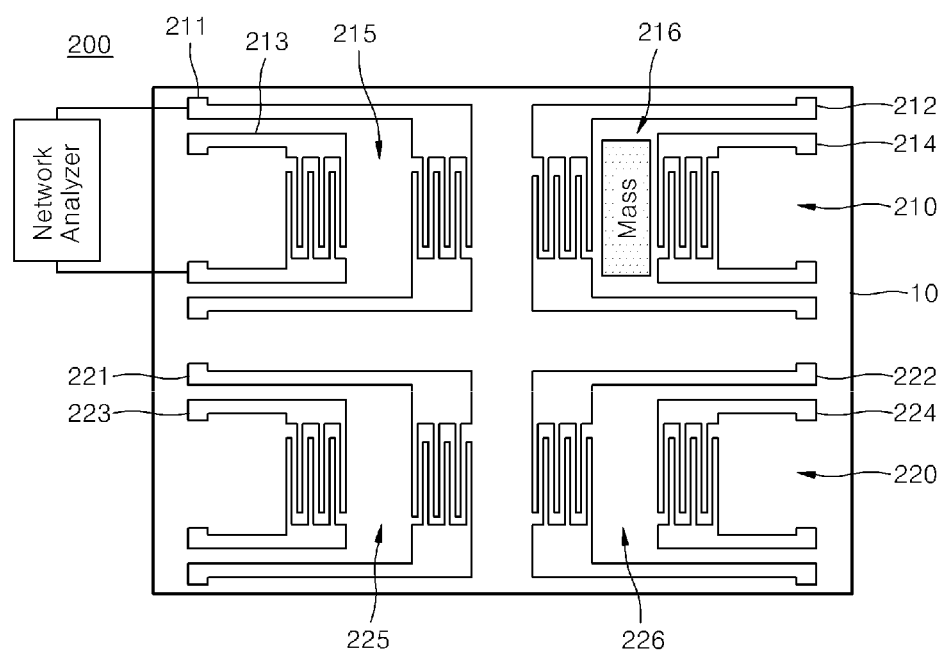
FIG. 9 is a schematic plan view of an arrangement for checking operating characteristics of the SAW array sensor illustrated in FIG. 5.
Figure 10:
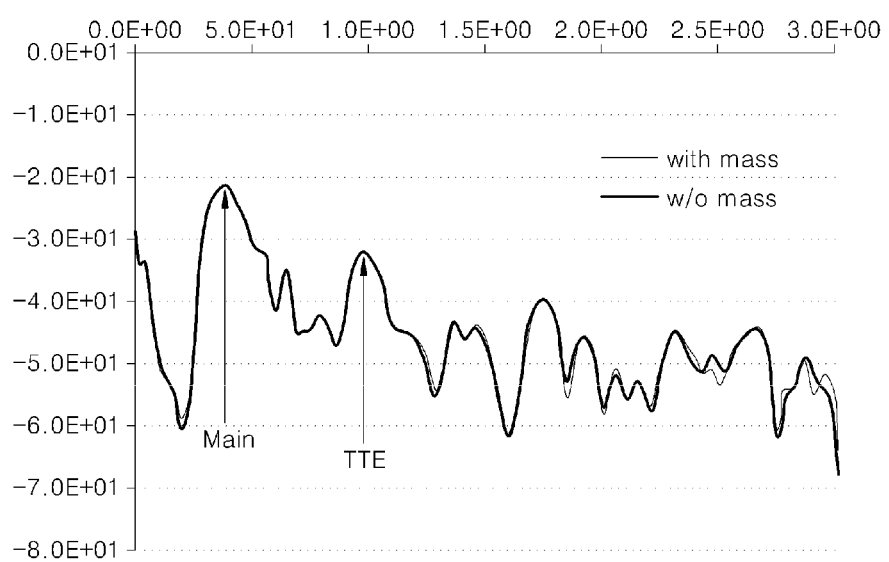
FIG. 10 is a graph showing operating characteristics of a SAW array sensor according to the arrangement of FIG. 9.

FIGS. 7 through 10 illustrate operating characteristics of the above-described SAW array sensors 100 of FIGS. 4 and 200 of FIG. 5. FIG. 7 is a schematic plan view of an arrangement for checking operating characteristics of the SAW array sensor 100 illustrated in FIG. 4. FIG. 8 is a graph showing operating characteristics of a SAW array sensor according to the arrangement of FIG. 7. FIG. 9 is a schematic plan view of an arrangement for checking operating characteristics of the SAW array sensor 200 illustrated in FIG. 5. FIG. 10 is a graph showing operating characteristics of a SAW array sensor 200 according to the arrangement of FIG. 9.

Referring to FIG. 7, a network analyzer is connected between the input IDT 111 and the first output IDT 112 so as to measure an insertion loss of the SAW that reaches the first output IDT 112 from the input IDT 111. For example, in order to check the effect of a reflected wave in the second output IDT 113, an insertion loss between the input IDT 111 and the first output IDT 112 is first measured without any substance or mass on the second delay line 115 between the input IDT 111 and the second output IDT 113. Subsequently, an insertion loss between the input IDT 111 and the first output IDT 112 is measured by putting an object having a predetermined mass on the second delay line 115.

FIG. 8 is a graph showing the result of measurement of the insertion loss. As shown in FIG. 8, there is no difference in the TTE signal at the second peak with and without the mass on the second delay line 115. Thus, cross-talk caused by the reflected wave that passes through the second delay line 115 is effectively removed so that a change in the TTE signal in the second delay line 115 does not affect measuring of a change in the TTE signal in the first delay line 114.

Referring to FIG. 9, a network analyzer is connected between the first input IDT 211 and the first output IDT 213 so as to measure an insertion loss of the SAW that reaches the first output IDT 213 from the first input IDT 211. Here, in order to check the effect of the SAW that passes through the second input IDT 212 and the second delay line 216, the insertion loss is first measured without a substance or mass on the second delay line 216, then an insertion loss between the first input IDT 211 and the first output IDT 213 is measured by putting an object having a predetermined mass on the second delay line 216.

FIG. 10 is a graph of the result of measurement of the insertion loss. As shown in FIG. 10, even in this case, there is hardly a difference in the TTE signal at the second peak with and without the mass on the second delay line 216. Thus, cross-talk caused by the SAW generated in the second input IDT 212 or the reflected wave that passes through the second delay line 216 is effectively removed so that a change in the TTE signal in the second delay line 216 does not affect measuring of a change in the TTE signal in the first delay line 215.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A surface acoustic wave (SAW) array sensor comprising:
   an input interdigital transducer (IDT) disposed on a piezoelectric substrate;
   first and second output IDTs disposed on the piezoelectric substrate and positioned on opposite sides of the input IDT;
   a first delay line between the input IDT and the first output IDT; and
   a second delay line between the input IDT and the second output IDT,
   wherein the first and second delay lines have different lengths configured to prevent any SAW reflected off either of the first and second output IDTs from interfering with a triple transient echo (TTE) measured at either one of the first and second output IDTs.

2. The SAW array sensor of claim 1, wherein the input IDT, the first and second output IDTs, and the first and second delay lines are aligned with one another in the traveling direction of a SAW from the input IDT to the output IDTs.

3. The SAW array sensor of claim 1, wherein a receptor that specifically binds with a target material is disposed on each of the first and second delay lines.

4. The SAW array sensor of claim 1, comprising a plurality of SAW sensor units that are arranged on a single piezoelectric substrate, wherein each of the plurality of SAW sensor units comprise:
   an input IDT;
   first and second output IDTs; and
   first and second delay lines,
   wherein the input IDT, first and second output IDTs, and first and second delay lines of each SAW sensor unit are aligned with one another in the travelling direction of a SAW.

5. The SAW array sensor of claim 4, wherein the plurality of SAW sensor units are arranged adjacent to one another in a direction generally perpendicular to the traveling direction of the SAW.

6. The SAW array sensor of claim 4, wherein a receptor that specifically binds a target material is disposed in each of the first and second delay lines of the plurality of SAW sensor units.

7. The SAW array sensor of claim 4, wherein the first delay lines of adjacent sensor units have different lengths, and the second delay lines of adjacent sensor units have different lengths.

8. A surface acoustic wave (SAW) array sensor comprising:
   first and second input interdigital transducers (IDTs) positioned on a piezoelectric substrate and facing each other;
   a first output IDT that is disposed on the piezoelectric substrate adjacent to the first input IDT and a second output IDT that is disposed on the piezoelectric substrate adjacent the second input IDT; wherein the first and second input IDTs are positioned between the first and second output IDTs;
   a first delay line between the first input IDT and the first output IDT; and a second delay line between the second input IDT and the second output IDT, wherein the first and second input IDTs are configured so that a SAW generated in the first input IDT and a SAW generated in the second input IDT are 180 degrees out of phase so that the SAW generated in the first input IDT and the SAW generated in the second input IDT are cancelled out at the location between the first input IDT and the second input IDT.

9. The SAW array sensor of claim 8, wherein the first input IDT and the second input IDT are axially symmetric to each other, and voltages having same polarities are applied to electrodes disposed at same sides of the first input IDT and the second input IDT relative to a line bisecting the IDTs in a direction parallel to SAW propagation.

10. The SAW array sensor of claim 8, wherein the first input IDT and the second input IDT are rotational symmetric about each other, and voltages having different polarities are applied to electrodes disposed at same sides of the first input IDT and the second input IDT relative to a line bisecting the IDTs in a direction parallel to SAW propagation.

11. The SAW array sensor of claim 8, wherein the first and second delay lines have different lengths.

12. The SAW array sensor of claim 8, wherein a receptor having a specific binding with a target material in a sample is disposed on each of the first and second delay lines.

13. The SAW array sensor of claim 8, wherein the first and second input IDTs, the first and second output IDTs, and the first and second delay lines are aligned with one another along a traveling direction of a SAW.

14. The SAW array sensor of claim 8, wherein the SAW array sensor comprises a plurality of SAW sensor units that are arranged on a single piezoelectric substrate, wherein each of the plurality of SAW sensor units comprises:

first and second input interdigital transducers (IDTs) positioned on a piezoelectric substrate and facing each other;

a first output IDT that is disposed on the piezoelectric substrate adjacent to the first input IDT and a second output IDT that is disposed on the piezoelectric substrate adjacent the second input IDT; wherein the first and second input IDTs are positioned between the first and second output IDTs;

a first delay line between the first input IDT and the first output IDT; and a second delay line between the second input IDT and the second output IDT.

15. The SAW array sensor of claim 14, wherein the plurality of SAW sensor units are arranged adjacent to one another along a direction generally perpendicular to the traveling direction of the SAW.

16. The SAW array sensor of claim 14, wherein a receptor that specifically binds a target material in a sample is disposed on each of the first and second delay lines of the plurality of SAW sensor units.

17. The SAW array sensor of claim 14, wherein the first delay line of a SAW sensor unit has a length that is different from that of the second delay line.

18. The SAW array sensor of claim 17, wherein the first delay lines of adjacent sensor units have different lengths, and the second delay lines of adjacent sensor units have different lengths.

19. The SAW array sensor of claim 14, wherein the first and second input IDTs are separated by a distance, and the distance between the first and second input IDTs of adjacent SAW sensor units is different.

* * * * *